US010556393B2

(12) United States Patent
Judd et al.

(10) Patent No.: US 10,556,393 B2
(45) Date of Patent: Feb. 11, 2020

(54) MONITORING OF CURE STATE THROUGH THE USE OF MICROWAVES

(71) Applicant: Compagnie Generale des Etablissements Michelin, Clermont-Ferrand (FR)

(72) Inventors: David Judd, Mauldin, SC (US); Frank Gramling, Simpsonville, SC (US); Reza Zoughi, Wildwood, MO (US); Mohammad Tayeb Ghasr, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 16/318,237

(22) PCT Filed: Jul. 18, 2017

(86) PCT No.: PCT/US2017/042490
§ 371 (c)(1),
(2) Date: Jan. 16, 2019

(87) PCT Pub. No.: WO2018/017516
PCT Pub. Date: Jan. 25, 2018

(65) Prior Publication Data
US 2019/0160770 A1  May 30, 2019

Related U.S. Application Data

(63) Continuation of application No. PCT/US2016/042748, filed on Jul. 18, 2016.

(51) Int. Cl.
*B29D 30/06* (2006.01)
*B29C 35/02* (2006.01)
(Continued)

(52) U.S. Cl.
CPC ...... *B29D 30/0662* (2013.01); *B29C 35/0294* (2013.01); *B29C 35/0288* (2013.01);
(Continued)

(58) Field of Classification Search
CPC ........ B29D 30/0662; B29D 2030/0674; B29D 2030/0675; B29C 35/0288; B29C 2035/0855; G01N 22/00
See application file for complete search history.

(56) References Cited

U.S. PATENT DOCUMENTS

| 3,397,583 A | 8/1968 | Sperberg | |
| 3,980,743 A * | 9/1976 | Smith | B29C 35/0288 264/408 |

(Continued)

OTHER PUBLICATIONS

European Patent Office; International Search Report and Written Opinion for patent application PCT/US2016/042748; dated Mar. 17, 2017; Publisher: European Patent Office, Rijswijk, Netherlands, pp. 1-11, enclosed.

(Continued)

*Primary Examiner* — James P Mackey
(74) *Attorney, Agent, or Firm* — Neal P. Pierotti (57) ABSTRACT

A method of manufacturing a tire is provided that includes curing the tire (10) in a curing press (12) and applying microwave energy at a given frequency band into the tire. The interaction between the microwave energy and the tire is monitored to obtain a complex reflection coefficient. A root-mean-squared error is calculated using the measured complex reflection coefficient and a reference reflection coefficient. The reference reflection coefficient is from a fully cured tire made from the same material as the tire. Continuous monitoring of the interaction takes place to obtain the complex reflection coefficient along with continuous calculation of the root-mean-squared error at different times during the curing of the tire in the curing press. The calculated root-mean-squared errors are used to determine whether to stop the curing of the tire in the curing press.

15 Claims, 4 Drawing Sheets

(51) Int. Cl.
 *B29C 35/08* (2006.01)
 *G01N 22/00* (2006.01)
(52) U.S. Cl.
 CPC ........... *B29C 2035/0855* (2013.01); *B29D 2030/0674* (2013.01); *B29D 2030/0675* (2013.01); *B29D 2030/0677* (2013.01); *G01N 22/00* (2013.01)

(56) References Cited

U.S. PATENT DOCUMENTS

| | | | |
|---|---|---|---|
| 5,233,306 A | | 8/1993 | Misra |
| 5,486,319 A | | 12/1996 | Stone |
| 5,648,038 A | * | 7/1997 | Fathi ............ G01N 22/00 264/40.1 |
| 5,721,286 A | * | 2/1998 | Lauf ............ H05B 6/686 522/1 |
| 2003/0234459 A1 | | 12/2003 | Nandu |
| 2004/0199350 A1 | | 10/2004 | Blackham |
| 2011/0043223 A1 | | 2/2011 | Canos Marin et al. |
| 2016/0047753 A1 | | 8/2016 | Zeiss |

OTHER PUBLICATIONS

European Patent Office; International Search Report and Written Opinion for patent application PCT/US2017/042490; dated Oct. 13, 2017; Publisher: European Patent Office, Rijswijk, Netherlands, pp. 1-11, enclosed.

* cited by examiner

MONITORING OF CURE STATE THROUGH THE USE OF MICROWAVES

CROSS-REFERENCE TO RELATED APPLICATIONS

The present application is a 35 U.S.C. § 371 application of PCT/US17/42490 filed on Jul. 18, 2017 and entitled "Monitoring of Cure State Through the Use of Microwaves." PCT/US17/42490 claims the benefit of PCT/US16/42748 filed on Jul. 18, 2016 and entitled "Monitoring of Cure State Through the Use of Microwaves." PCT/US16/42748 and PCT/US17/42490 are both incorporated by reference herein in their entireties for all purposes.

FIELD OF THE INVENTION

The subject matter of the present invention relates to the monitoring of cure state through the use of microwaves. More particularly, the present application involves monitoring the curing of a tire by the application of microwave energy to the tire during curing and study of the interaction between the microwave energy and the tire.

BACKGROUND OF THE INVENTION

The production of tires involves the step of placing a green/uncured tire into a curing press and applying heat and pressure for a sufficient amount of time in order to achieve cure. If the tire is under cured in the press, air bubbles or other non-uniformities may develop in the tire and result in a final product with weakened areas and undesired construction. Knowledge of exactly how much time is needed to completely cure a tire may not be able to be achieved because of variations in tire materials and in the tire building process. These variations cause tires to require different amounts of cure time. In order to ensure the tires are properly cured, a safety factor is introduced into the curing stage of the tire. In this regard, extra time is added to the amount of time all tires are cured so that any variation in the tire necessitating a different amount of cure time is taken into account. The downside of adding additional cure time into the process is that this cure time may not be necessary and thus unnecessary time is wasted by keeping the tire at the curing stage. As the curing stage is typically a bottleneck in the tire production process, any wasted time at this stage of manufacture is undesirable. As such, a way of monitoring the tire to determine whether it has achieved cure would help in achieving better through put at the curing stage.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

The use of identical or similar reference numerals in different figures denotes identical or similar features.

DETAILED DESCRIPTION OF THE INVENTION

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

A method of determining whether a tire 10 is cured is provided that involves the application of microwave energy into the tire 10 along with associated monitoring of the interaction between the tire 10 and this applied microwave energy. A complex reflection coefficient is obtained via the microwave/tire 10 monitoring, and a root-mean-squared error value is calculated. The calculation of the root-mean-squared error includes the complex reflection coefficient, and includes a reference reflection coefficient that is from a fully cured tire 10 of the same material. The root-mean-squared error is monitored during the curing of the tire 10 in the curing press 12, and it is used to determine whether the tire 10 has been appropriately cured. In this manner, variations in the tire 10 building process can be accounted for in tracking the cure state of the tire 10 because the curing of the tire 10 is monitored on an individual level. The throughput of the curing press 12 can be optimized and the overall cure time reduced for tires 10 running through the curing press 12.

Figure 1:
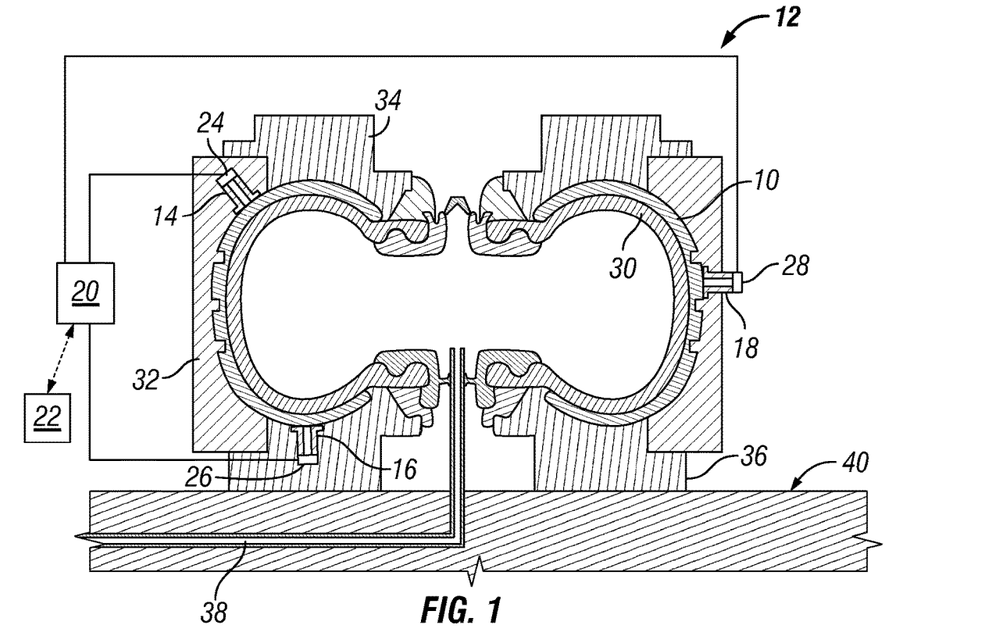
FIG. 1 is a cross-sectional view of a tire in a mold with waveguide probes positioned in the mold and in communication with a vector network analyzer and microprocessor.

FIG. 1 illustrates a curing press 12 that is used to apply heat and pressure to a tire 10 over a certain amount of time in order to cure the tire 10. Once cured, the tire 10 is removed from the curing press 12 and moved downstream to the next stage of production. After removal, the tire 10 may still be warm and portions of the material making up the tire 10 may still cure for some amount of time even though pressure is no longer being applied to the tire 10. As such, the tire 10 may not be said to be fully cured upon exiting the curing press 12 because some curing still takes place afterwards. However, as used herein it is to be understood that the term curing refers to the curing of the tire 10 while located in the curing press 12, and such curing may be fully cured so that the tire 10 undergoes no further curing upon removal from the curing press 12, or such curing may be partial curing such that the tire 10 does undergo some further curing upon leaving the curing press 12.

The curing press 12 includes a sidewall segment 36 located on the ground 40, and oppositely disposed sidewall segments 34 located farther form the ground 40. A series of tread segments 32 are located circumferentially around the tire 10. The segments 32 and 34 may move in relation to the ground 40 and segment 36 to provide a space to allow the tire 10 to be placed inside of the curing press 12 and subsequently removed from the curing press 12. The curing press 12 also includes a bladder 30 that can be inflated, and possibly deflated, via an inflation line 38 in communication with a pressure source (not shown). During tire 10 curing, the bladder 30 is deflated and the tire 10 is placed onto the sidewall segment 36. The treat and sidewall segments 32 and 34 may be closed towards one another, and the bladder 30 can be inflated into its inflated orientation as shown in FIG. 1. Pressure from the segments 32, 34, and 36 applied to the outside of the tire 10 will be counteracted by pressure from the bladder 30 on the inside of the tire 10 to cause the tire 10 to have pressure applied to it during the curing process. Heat can be transferred through the segments 32, 34 and 36 via temperature probes in these segments 32, 34 and 36 or through the material making up the segments 32, 34 and 36 themselves.

A waveguide probe 14 is shown being located within the tread segment 32 so that it engages the outer surface of the tire 10 at a shoulder portion of the tire 10. Another waveguide probe 16 is located in sidewall segment 36 and engages the tire 10 at a bead portion of the tire 10. A further waveguide probe 18 is located in the tread segment 32 and engages the outer surface of the tread of the tire 10. The waveguide probes 14, 16 and 18 may engage the tire 10 as shown, or may be spaced from the tire 10 but directly face the tire 10 so that nothing is between them and the tire 10 in various embodiments. Further, although shown as being three in number, one, two, from 4-8, or up to 16 waveguide probes may be employed in various exemplary embodiments. Still further, other areas of the tire 10 may be associated with the waveguide probes instead of or in addition to those shown. Also, the waveguide probes 14, 16 and 18 could be located in any of the segments 32, 34 or 36 or even at locations of the curing press 12 that are not the segments 32, 34 or 36.

Microwave energy may be transferred through the various waveguide probes 14, 16 and 18 and into the tire 10. The microwave energy upon contacting the tire 10 will have a portion that is reflected back into the waveguide probes 14, 16 and 18 and a portion that permeates through the tire 10. Energy through the waveguide probes 14, 16 and 18 can be transferred back to a vector network analyzer 20 that is in communication with the waveguide probes 14, 16 and 18 to obtain their readings. The waveguide probe 14 may have an adapter 24 that functions to convert the received microwave energy into a signal capable of being used by the vector network analyzer 20 to determine a complex reflection coefficient. The waveguide probe 16 may have its own adapter 26, and waveguide probe 18 may have its own adapter 28 as well to convert received signals for input into the vector network analyzer 20.

The vector network analyzer 20 is in communication with the waveguide probes 14, 16 and 18 and may send data to and receive information from the waveguide probes 14, 16 and 18. The vector network analyzer 20 (VNA) is capable of measuring the complex reflection coefficient (magnitude and phase) of the tire 10 upon receiving the signal from the waveguide probes 14, 16 and 18. A processor 22 can be in communication with the vector network analyzer 20 and may function to perform calculations associated with the disclosed method. Alternatively, the vector network analyzer 20 itself may perform calculations on the computed complex reflection coefficients to determine the cure state of the tire 10.

Curing of the material making up the tire 10 causes the dielectric constant of the material to change as the material becomes more and more cured. The dielectric constant may sometimes be referred to as relative permittivity and may be the absolute permittivity of the material expressed as a ratio relative to the permittivity of vacuum. The dielectric constant is an intrinsic property of the material. A change in the dielectric constant of a material causes a change in the complex reflection coefficient of the material. The complex reflection coefficient may be measured by the method and this value can be manipulated through calculation to ascertain the cure state of the tire 10. When the microwave hits the tire 10, a portion of the microwave is reflected back off of the tire 10, and a portion of the microwave passes through the tire 10. The complex reflection coefficient may be thought of as a ratio of the reflected wave amplitude to the incident wave amplitude. The complex reflection coefficient can be expressed as a complex number. Additionally or alternatively, the complex reflection coefficient can be expressed as having magnitude and phase components.

During the curing process the waveguide probe 14 measures the microwave energy at its location at the tire 10 and transmits this information to the vector network analyzer 20 that establishes a measured complex reflection coefficient. The vector network analyzer 20 may obtain the measured complex reflection coefficient from the data supplied by the waveguide probe 14 in a variety of manners. In some instances, a forward-iterative optimization algorithm using an nlayer model is used to arrive at the complex reflection coefficient. With the complex reflection coefficient, a root-mean-squared error (RMSE) may next be calculated to ascertain the cure state of the material. To do this, a reference reflection coefficient must first be obtained. The reference reflection coefficient is the complex reflection coefficient obtained from a fully cured sample. With respect to the waveguide probe 14, a reference tire 10 that is fully cured may be measured at the same location as the location of the waveguide probe 14 on the tire 10. The reference tire 10 and the measured tire 10 are made of the same material so that they yield the same measured reflection coefficients depending upon their state of cure. The reference reflection coefficient can be an average of measurements from multiple reference tires 10 at the location in question.

The measured reflection coefficient $S_{11}$ and the reference reflection coefficient $S_{11ref}$ are used in the following equation to calculate the root-mean-squared error (RMSE) or $Error_{rms}$:

$$Error_{rms} = \sqrt{\frac{1}{nf} \sum_{f} |S_{11} - S_{11ref}|^2}$$

As the tire 10 cures, the root-mean-squared error can be calculated at various points in time. The time intervals can be evenly spaced or unevenly spaced. As the tire 10 cures, the root-mean-squared error will decrease at a generally constant rate. This rate of change may be linear or close to linear. Once the tire 10 reaches a fully cured state, the root-mean-squared error will level off in that it will change its slope or will no longer decrease but instead be a line moving forward in time. The plotted line of the root-mean-squared error of the tire 10 will thus exhibit a stabilization of the rate of change of the microwave energy when the tire 10 reaches a point of cure in the curing press 12. The method may recognize the tire 10 as being fully cured and then stop the curing of the tire 10 in the curing press 12 and remove the tire 10 for subsequent downstream processing. In some embodiments, once the fully cured state has been realized by monitoring of the root-mean-squared error, the method may continue to cure the tire 10 in the curing press 12 to ensure that the fully cured state is reached. This additional curing time may be referred to as a safety factor in the tire 10 curing. Once the fully cured state is realized, the method may then decide to stop the curing of the tire 10 in the curing press 12 by executing the additional curing to achieve the safety factor and then stopping the curing in the curing press 12. Additionally or alternatively, the method may denote the fully cured state in the curing press 12 by denoting a low error value of the root-mean-squared error. If the root-mean-squared error drops below a threshold value, the method will interpret this as the tire 10 being fully cured.

If the curing press 12 is outfitted with the additional waveguide probes 16 and 18, complex reflection coefficients from these locations can be obtained by the vector network analyzer 20 at different times during the tire 10 cure. Root-mean-squared errors may also be calculated at these locations associated with the additional waveguide probes 16 and 18. The fully cured state can be realized once all of the root-mean-squared errors from the various locations on the tire 10 stabilize and/or fall below a certain threshold value. In still other embodiments of the method, the various root-mean-squared errors that are obtained at a point in time from the various waveguide probes 14, 16 and 18 can be averaged to obtain an average root-mean-squared error that is then analyzed to determine whether its plot has stabilized over time and/or has fallen below a threshold value to determine the fully cured state.

Experiments have been conducted in carrying out the disclosed method. In this regard, two samples each of various rubber materials at different curing levels were provided as illustrated in Table #1.

TABLE #1

| Sample Detail | | | |
|---|---|---|---|
| Material Label # | t# | Curing Temperature | Curing Time (min) |
| 23203 | t70 | 150 degrees C. | 11 |
| 23203 | t80 | 150 degrees C. | 14 |
| 23203 | t90 | 150 degrees C. | 21 |
| 23203 | t100 | 150 degrees C. | 45 |
| 23204 | t70 | 150 degrees C. | 15 |
| 23204 | t80 | 150 degrees C. | 20 |
| 23204 | t90 | 150 degrees C. | 29 |
| 23204 | t100 | 150 degrees C. | 45 |
| 23555 | t70 | 150 degrees C. | 10 |
| 23555 | t80 | 150 degrees C. | 12 |
| 23555 | t90 | 150 degrees C. | 15 |
| 23555 | t100 | 150 degrees C. | 32 |
| 25610 | t70 | 150 degrees C. | 8 |
| 25610 | t80 | 150 degrees C. | 12 |
| 25610 | t90 | 150 degrees C. | 18 |
| 25610 | t100 | 150 degrees C. | 60 |

The material label numbers are different types of rubber that are made up of different components. The times such as # t70 mean that this particular sample was cured for 70 percent of its fully cured state in the curing press 12. The #t100 means that the particular sample was in fact fully cured. The curing times show the amount of time each of the samples was cured in the curing press 12. As may be seen, different types of rubber denoted by the material label numbers show that different curing times are needed in order to fully cure the sample. It is thus the case that the curing time needed is dependent upon the material making up the particular sample/tire 10. The material samples tested were square samples all having generally the same size.

The microwave energy imparted onto the tire 10 can be at various frequency bands, and it may be the case that one type of microwave energy would work better for a particular material than a different type of microwave energy. In this regard, the method may be optimized so that the best type of microwave energy imparted onto the material making up the tire 10 is used so that the best root-mean-squared results are obtained to determine the cure state of the tire 10. For experimental purposes, multiple types of microwave energy was imparted onto the various samples to study how the material reacts to the different types. The microwave energy imparted was K-band (18-26.5 gigahertz), X-band (8.2-12.4 gigahertz), J-band (5.85-8.2 gigahertz), and S-band (2.6-3.95 gigahertz). The use of different bands of microwave energy for measurement may require different sized waveguide proves 14 and adapters 24, and if these components are different sized then it may be the case that the same number of measurements at different locations on the samples cannot be obtained for all of the microwave bands. This is because an edge effect that distorts the received microwave energy can occur and the different sized equipment is thus sensitive to this edge effect.

Figure 2:
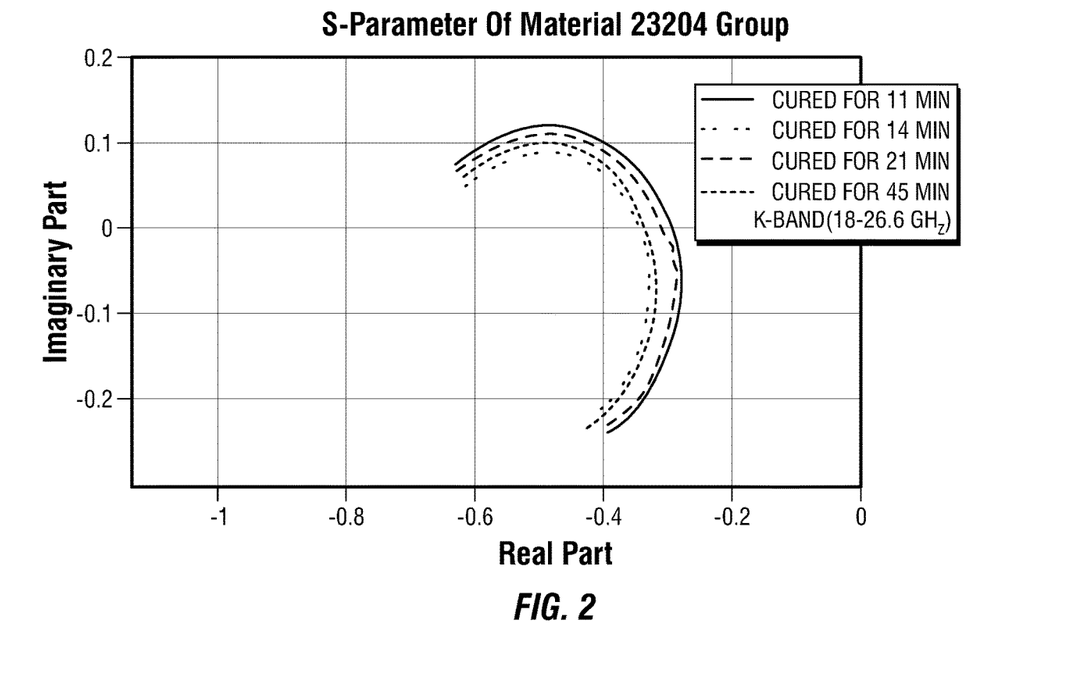
FIG. 2 is a plot of a measured complex reflection coefficient from a material 23204 group sample.
Figure 3:
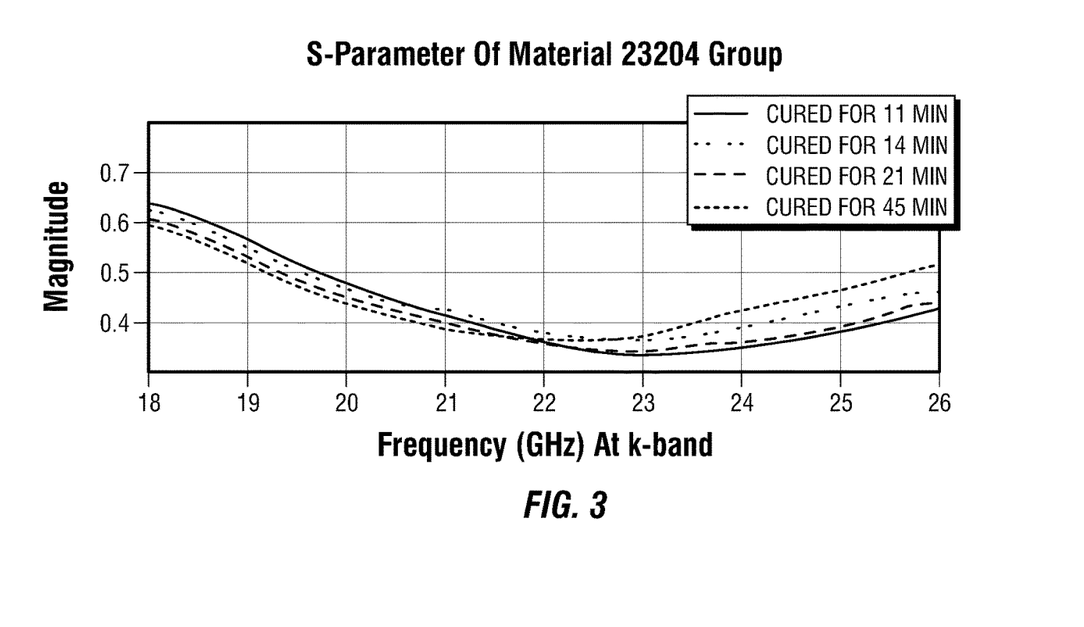
FIG. 3 is a plot of the magnitude of the measured complex reflection coefficient of the measured sample from FIG. 2.
Figure 4:
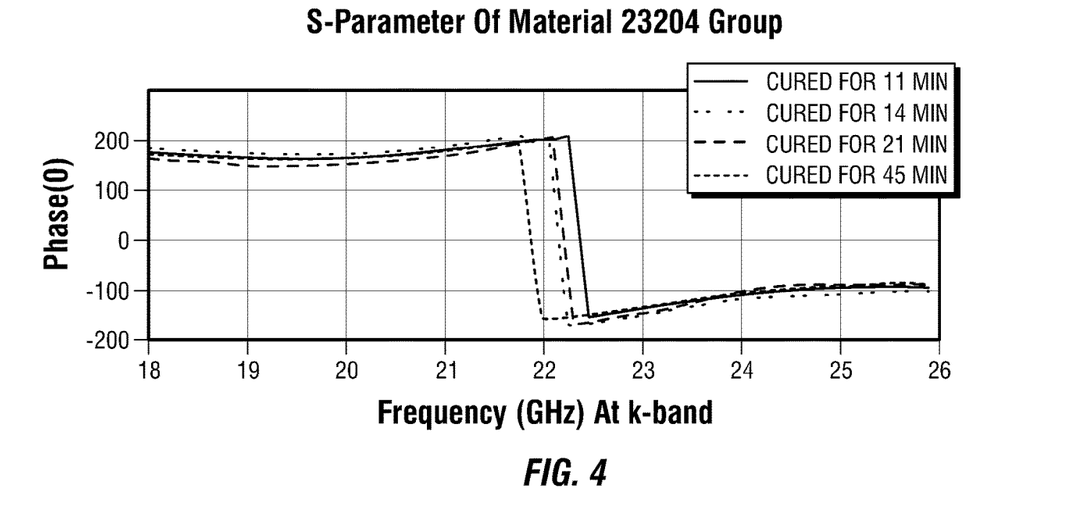
FIG. 4 is a plot of the phase of the measured complex reflection coefficient of the measured sample from FIG. 2.

FIG. 2 shows the complex reflection coefficient obtained from material sample 23204 using K-band microwave energy. The real and imaginary portions of the complex number making up the reflection coefficient is graphed for the four cured times given on the four different samples at a corresponding location on each of the four samples at different curing rates. The change at the different levels of cure is small, but it can be measured. The complex reflection coefficient can also be expressed as having a magnitude and phase, and this illustration of the complex reflection coefficient at the four different cured times of the four samples of the 23204 material at a corresponding location is shown with reference to FIGS. 3 and 4.

The size of the waveguide prove 14 and adapter 24 with the K-band allowed for seven locations on the sample to be measured. As such, seven different complex reflection coefficients can be obtained at each one of the cure states provided. In addition, two samples from table 1 were provided for each one of the rows, and the second sample of the 23204 material provided at each one of the four cure times were additionally measured to result in 14 different complex reflection coefficients obtained for each cure state.

Each one of the complex reflection coefficients $S_{11}$ are used in conjunction with the reference reflection coefficient $S_{11ref}$ to obtain the root-mean-squared error (RMSE) or $Error_{rms}$ at each point in time t70, t80, t90 or t100. As fourteen points are obtained at each point in time, fourteen root-mean-squared errors are calculated. From this, the mean of the fourteen root-mean-squared errors is calculated by adding up the fourteen values and then dividing this result by fourteen, which is the number of values added. In some embodiments, the standard deviation of the fourteen root-mean-squared error numbers can be calculated. The standard deviation can be obtained from the following formula:

$$\sigma = \sqrt{\frac{1}{N}\sum_{i=1}^{N}(x_i - \mu)^2}$$

Figure 5:
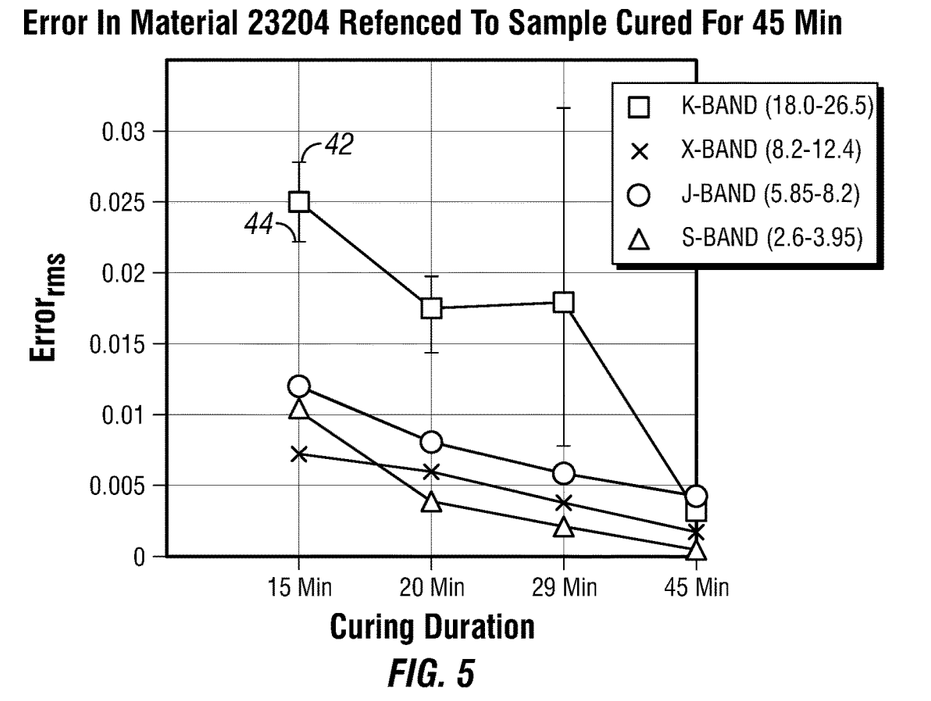
FIG. 5 is a plot of the root mean squared error measured in four different microwave bands for material 23204.

With reference to FIG. 5, the K-band measurements for material 23204 is shown at t70 which is at 15 minutes of cure time. The mean is from the fourteen measurements of the root-mean-squared error value and is at 0.025. The standard deviation was also calculated at the K-band and is represented at the 15 minute mark by the standard deviation high 42 mark, located at approximately 0.032 root-mean-squared, and the standard deviation low 44 reference mark, located at approximately 0.022 root-mean-squared error.

The root-mean-squared error can be calculated at the 20 minutes mark for the t80 samples that again generate fourteen complex reflection coefficients. The root-mean-squared calculation for time t80 will use the same reference reflection coefficient $S_{11ref}$ as that at the t70 time. In fact, all calculations of the root-mean-squared error will use the same reference reflection coefficient $S_{11ref}$ at all times. However, different reference reflection coefficient $S_{11ref}$ values may be found across different points of the sample as this value may be different at different points on the sample/tire 10. The mean of the fourteen calculated root-mean-squared error values will be found and is 0.017, and the standard deviation of these fourteen values can be again calculated and are shown in FIG. 5 as the horizontal lines above and below the mean. This process may be repeated for the t90 values at the 29 minute cured samples, and the mean and standard deviations are again shown in FIG. 5. Study of the K-band calculations of the root-mean-squared error values in FIG. 5 shows that they decrease from t70 to t80, but remain essentially the same between t80 to t90. The root-mean-squared error does drop from t90 at 29 minutes to t100 at the 45 minute cured sample. There is a general downward trend of the root-mean-squared error value as the cure times increase, and this downward trend can be used to recognize a fully cured state.

The same process can be repeated with the same 23204 samples although using different microwave bands as shown in FIG. 5. The X-band and its associated waveguide probe 14 and adapter 24 are capable of measuring five different locations on the 23204 samples due to the difference in size from the K-band equipment and the desire to reduce or eliminate edge effect. Since two samples are present, ten complex reflection coefficients can be obtained at each time provided. The means of the root-mean-squared errors may be calculated in the same manner as previously described with respect to the K-band numbers, although with the X-band ten instead of fourteen values are employed. The resulting means are plotted on the graph of FIG. 5, and the standard deviations are not shown for sake of clarity on the graph but could be included if desired in other plots. The same calculations can be done for the J-band although with the J-band only three locations on the 23204 are measured due to the size difference in equipment, resulting in six measurements taken at each point from which the mean of the root-mean-squared error values are derived. The S-band can also be done although it is too large to measure different locations on the 23204 sample. Instead, three measurements at the center can be executed to again result in six total complex reflection coefficient measurements taken at each time. The root-mean-squared error values are plotted on the graph for the S-band.

As shown in FIG. 5, the general trend of the root-mean-squared error values is downward as the 23204 samples approach the fully cured state. To determine the fully cured state, a threshold value can be set, for example at 0.005. Once the root-mean-squared error value drops below 0.005 the sample/tire 10 is designated as being fully cured. Additionally or alternatively, a flattening out or changing of the rate of change of the plot of root-mean-squared error values can designate the fully cured condition. The flattening out could be when the root-mean-squared error value does not change from one point in time to the next to next several subsequent points in time. This is not seen in FIG. 5 due to the fact that data in only four different points in time were plotted. However, a greater number of data points found at points closer in time may reveal a flattened root-mean-square error value and thus a designation of the fully cured state.

A slope or rate of change of the root-mean-squared error values can be found at points before the fully cured state. If this slope or rate of change of the plot changes, then the fully cured state can be established. The J-band results show a change in the rate of change of the plot from the 29-45 minute mark that is different than the rate of change or slope from the 20-29 minute mark. The fully cured state may be identified by this rate of change. In other manners, additional data points at additional time points can be found in the plot to better capture or see a change in the slope or rate of change of the root-mean-squared error values. It may be the case that some of the microwave bands do not work well for the material in that particular sample. As shown, the K-band appears not to show a downward slope of the root-mean-squared error value between the 20-29 minute marks so the K-band may not be an optimum microwave energy band to use with the 23204 sample. As some bands are better than others depending upon the material analyzed, an optimal microwave band for each sample/tire 10 type can be selected from the reactions shown of all the variously used bands.

Figure 6:
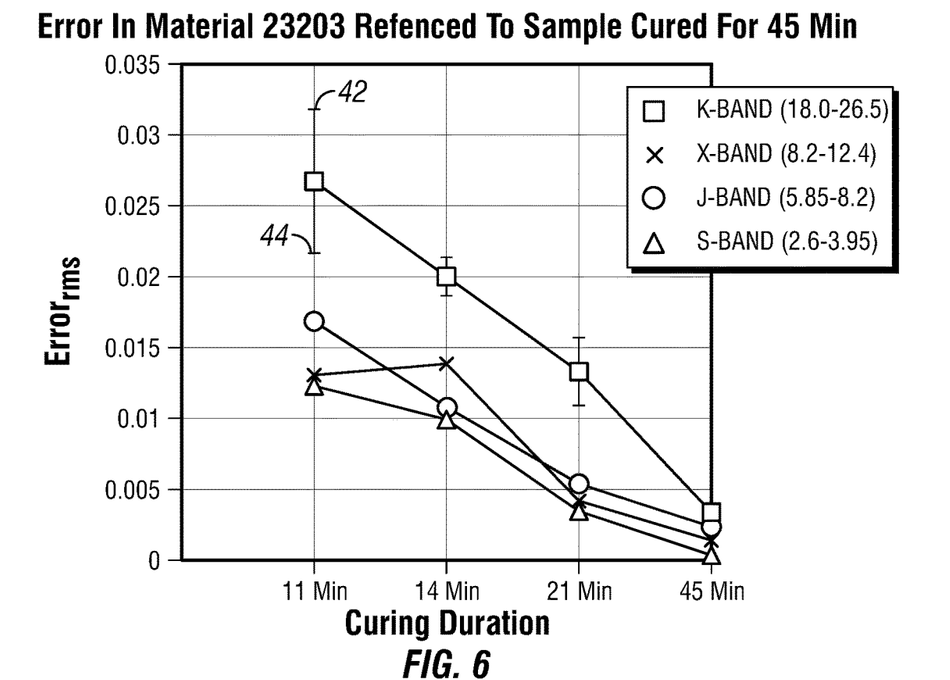
FIG. 6 is a plot of the root mean squared error measured in four different microwave bands for material 23203.
Figure 7:
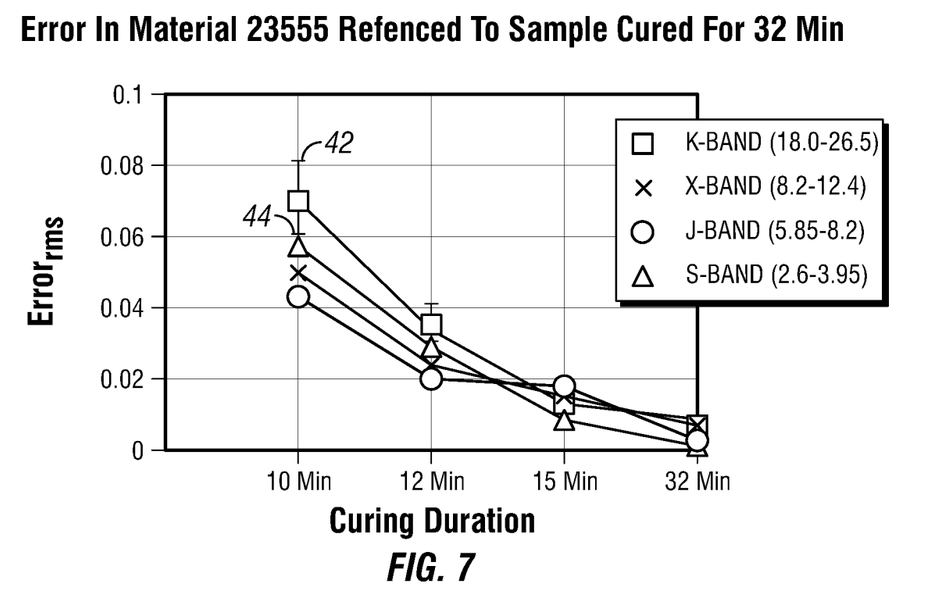
FIG. 7 is a plot of the root mean squared error measured in four different microwave bands for material 23555.

The other samples of the material/tire 10 were analyzed in the same manner. FIG. 6 shows the plot of all four microwave bands for the 23203 material. The means of the root-mean-squared error values are calculated in the same manner as previously discussed with respect to the 23204 material. The K-band is shown as yielding a good indication with respect to slope or rate of change to discover the fully cured state. The slope of the root-mean-squared value is consistent from t70 at 11 minutes to t90 at 21 minutes. However, the slope and rate of change changes between the t90 and t100 times from 21 to 45 minutes so that this slope and rate of change is different at this time interval than from the 11 minutes to 21 minute interval. This slope or rate of change shows the fully cured condition is indicated. Additionally or alternatively, the K-band shows a threshold of 0.005 below which the fully cured state is realized and this threshold may be used to likewise identify the fully cured state. The X, J and S-bands are not very strong indicators of the threshold as they are likewise below or just above the threshold at the t90 time. The 23555 material sample is shown in FIG. 7 again at the four microwave bands with the root-mean-squared errors calculated in the same manner previously discussed. The slope can be seen as leveling off for the K-band as it approached the fully cured state. In this regard, the slop from the 15-32 minute mark is different and flatter than the slop from the 10-15 minute marks to show a rate of change adjustment. The thresholds, if used, may be at a 0.01 root-mean-squared error value below which all four bands tend to show a fully cured state.

Figure 8:
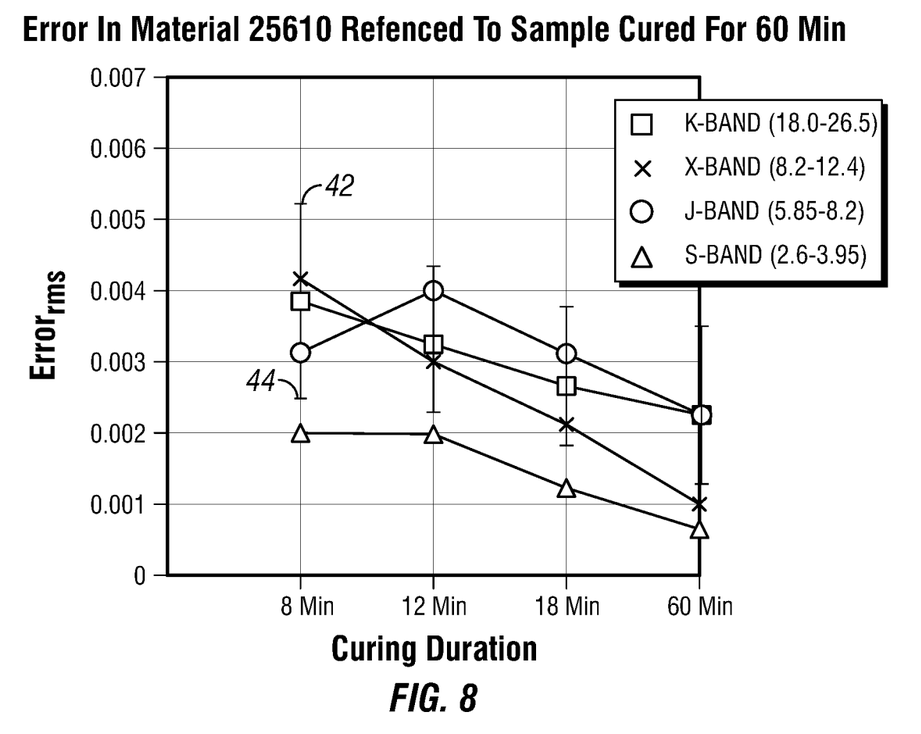
FIG. 8 is a plot of the root mean squared error measured in four different microwave bands for material 25610.

FIG. 8 shows the root-mean-squared plot versus time for the 25610 samples again over the four microwave bands. The K-band shows a leveling off from 18-60 minutes as opposed to the different slope or rate of change from the 8-18 minute mark. This microwave band may be the optimal band to use for detection of the fully cured state if using a slope or rate of change difference. The threshold values can be used to identify the fully cured state as well. For example, if using the S-band, a threshold of below 0.001 can be used, and if using the X-band a threshold of below 0.002 can be used. Different threshold can be used for the K and J-bands as the K-band may have a threshold of below 0.0025, while the J-band can have a threshold of below 0.003 to identify the fully cured condition. If a leveling off is desired to be used to identify the fully cured condition, the plot can be evaluated to determine when the root-mean-squared error does not change from one point in time to another and at this state the fully cured condition can be determined.

While the present subject matter has been described in detail with respect to specific embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method of manufacturing a tire, comprising:
    curing the tire in a curing press;
    applying microwave energy at a given frequency band into the tire during the curing of the tire;
    monitoring the interaction between the microwave energy and the tire to obtain a complex reflection coefficient;
    calculating a root-mean-squared error using the measured complex reflection coefficient and a reference reflection coefficient, wherein the reference reflection coefficient is from a fully cured tire made from the same material as the tire;
    continuing to monitor the interaction to obtain the complex reflection coefficient and continuing to calculate the root-mean-squared error at different times during the curing of the tire in the curing press; and
    using the calculated root-mean-squared errors to determine whether to stop the curing of the tire in the curing press.

2. The method of manufacturing as set forth in claim 1, wherein the determination of whether to stop the curing of the tire in the curing press is made when one of the calculated root-mean-squared errors falls below a threshold value.

3. The method of manufacturing as set forth in claim 1, wherein the calculated root-mean-squared errors decrease at a rate of change as the tire is cured in the curing press, wherein the determination of whether to stop the curing of the tire in the curing press is made when the rate of change of the calculated root-mean-squared errors levels off.

4. The method of manufacturing as set forth in claim 3, wherein the leveling off occurs when the rate of change of the calculated root-mean-squared errors becomes zero.

5. The method of manufacturing as set forth in claim 1, wherein the microwave energy is in the X-band ranging from 8.2-12.4 GHz.

6. The method of manufacturing as set forth in claim 1, wherein the microwave energy is in the K-band ranging from 18-26.5 GHz.

7. The method of manufacturing as set forth in claim 1, wherein the microwave energy is in the J-band ranging from 5.85-8.2 GHz.

8. The method of manufacturing as set forth in claim 1, wherein the microwave energy is in the S-band ranging from 2.6-3.95 GHz.

9. The method of manufacturing as set forth in claim 1, wherein the applying the microwave energy at the given frequency band into the tire during the curing of the tire is a first frequency band; further comprising:
    applying microwave energy at a given second frequency band into the tire during the curing of the tire;
    monitoring the interaction between the microwave energy at the second frequency band and the tire to obtain a second complex reflection coefficient;
    calculating a second root-mean-squared error using the measured second complex reflection coefficient and a reference reflection coefficient, wherein the reference reflection coefficient is from a fully cured tire made from the same material as the tire from the microwave energy at the second frequency band;
    continuing to monitor the interaction to obtain the second complex reflection coefficient and continuing to calculate the second root-mean-squared error at different times during the curing of the tire in the curing press; and
    using the calculated second root-mean-squared errors to determine whether to stop the curing of the tire in the curing press.

10. The method of manufacturing as set forth claim 1, wherein during the monitoring of the interaction between the microwave energy and the tire a waveguide probe collects reflected microwave energy from the tire and information from the waveguide probe is sent to a vector network analyzer to obtain the complex reflection coefficient.

11. The method of manufacturing as set forth in claim 1, wherein the root-mean-squared error is calculated using the following formula:

$$Error_{rms} = \sqrt{\frac{1}{nf}\sum_{f}|S_{11} - S_{11ref}|^2}$$

wherein $S_{11}$ is the complex reflection coefficient; and
wherein $S_{11ref}$ is the reference reflection coefficient.

12. The method of manufacturing as set forth in claim 1, wherein multiple complex reflection coefficients are obtained during the monitoring that are at multiple locations on the tire at one point in time;
    wherein multiple root-mean-squared errors are obtained during the calculating using the multiple measured complex reflection coefficients and multiple reference reflection coefficients, wherein the multiple reference reflection coefficients are from the fully cured tire made from the same material at the multiple locations on the tire;
    wherein multiple complex reflection coefficients are obtained and multiple root-mean-squared errors are calculated during the continuing to monitor at different times during the curing of the tire in the curing press;
    wherein the multiple calculated root-mean-squared errors at different times are used in the using step to determine whether to stop the curing of the tire in the curing press.

13. The method of manufacturing as set forth in claim 12, further comprising calculating means of the multiple root-mean-squared errors at the various times, wherein the calculated means are used in the using step to determine whether to stop the curing of the tire in the curing press.

14. The method of manufacturing as set forth in claim 12, further comprising calculating the standard deviation of the multiple root-mean-squared errors at the various times.

15. The method of manufacturing as set forth in claim 1, further comprising stopping the curing of the tire in the curing press.

* * * * *